(12) United States Patent
Li et al.

(10) Patent No.: US 8,669,377 B2
(45) Date of Patent: Mar. 11, 2014

(54) **ANTI-HUMAN UROTHELIAL CARCINOMA OF SUPERCRITICAL CARBON DIOXIDE EXTRACT OF *CINNAMOMUM SUBAVENIUM*, AND THE PREPARATION PROCESS AND USES**

(75) Inventors: Jih-Heng Li, Taipei (TW); A-Mei Huang, Kaohsiung (TW); Chung-Yi Chen, Kaohsiung (TW); Pei-Jung Lien, Kaohsiung (TW); Chiung-Hui Liu, Nantou County (TW)

(73) Assignee: Kaohsiung Medical University (TW)

( * ) Notice: Subject to any disclaimer, the term of this patent is extended or adjusted under 35 U.S.C. 154(b) by 0 days.

(21) Appl. No.: 13/426,136

(22) Filed: Mar. 21, 2012

(65) Prior Publication Data

US 2013/0122110 A1    May 16, 2013

(30) Foreign Application Priority Data

Nov. 15, 2011  (TW) .............................. 100141688 A

(51) Int. Cl.
    *C07D 307/02*    (2006.01)
(52) U.S. Cl.
    USPC ......................................................... 549/295
(58) Field of Classification Search
    USPC ......................................................... 549/295
    See application file for complete search history.

(56) References Cited

U.S. PATENT DOCUMENTS

| | | | |
|---|---|---|---|
| 7,326,734 B2 | 2/2008 | Zi et al. | |
| 2009/0247480 A1 | 10/2009 | Tidmarsh | |
| 2011/0212194 A1 | 9/2011 | Wang et al. | |

FOREIGN PATENT DOCUMENTS

| | | |
|---|---|---|
| TW | 200914036 | 4/2009 |
| TW | 200924788 | 6/2009 |
| WO | 0072861 A1 | 12/2000 |

OTHER PUBLICATIONS

Zubrick, The Organic Chem Lab Survivial Manaual, 1984, p. 111-127, 193-195.*
Liu et al., "Subamolide A, a component isolated from *Cinnamomum subavenium*, induces apoptosis mediated by mitochondria-dependent, p53 and ERK1/2 pathways in human urothelial carcinoma cell line NTUB1," Journal of Ethnopharmacology (2011) 137:503-511.
Chen et al., "Cytotoxic Constituents of the Stems of *Cinnamomum subavenium*," J. Nat. Prod. 2007, 70, 103-106.
Shen et al., "Isolinderanolide B, a Butanolide Extracted from the Stems of *Cinnamomum subavenium*, Inhibits Proliferation of T24 Human Bladder Cancer Cells by Blocking Cell Cycle Progression and Inducing Apoptosis," Integr Cancer Ther 2011 10:350.

* cited by examiner

*Primary Examiner* — Nizal Chandrakumar
(74) *Attorney, Agent, or Firm* — Volpe and Koenig, P.C.

(57) ABSTRACT

What is disclosed in the invention is a preparation method of a supercritical *Cinnamomum subavenium* extract, which is made from the material, the dried stem of *C. subavenium*. The extract is obtained by extracting *C. subavenium* which is pulverized as particles with supercritical carbon dioxide fluid. The *C. subavenium* extract or its active ingredient, subamolide A, can be used to inhibit the growth of human urothelial carcinoma cell lines. In addition, the *C. subavenium* extract (or subamolide A) is able to synergistically inhibit the growth of human urothelial carcinoma cell lines with cisplatin (CDDP) or gemcitabine (Gem). Therefore, the *C. subavenium* extract (or subamolide A) can be an anticancer drug alone, or forms a pharmaceutical composition with CDDP (or Gem) to treat with cancers in respect of urinary system.

6 Claims, 9 Drawing Sheets

US 8,669,377 B2

ANTI-HUMAN UROTHELIAL CARCINOMA OF SUPERCRITICAL CARBON DIOXIDE EXTRACT OF *CINNAMOMUM SUBAVENIUM*, AND THE PREPARATION PROCESS AND USES

CROSS-REFERENCE TO RELATED APPLICATION AND CLAIM OF PRIORITY

The application claims the benefit of Taiwan Patent Application No. 100141688, filed on Nov. 15, 2011, in the Taiwan Intellectual Property Office, the disclosures of which are incorporated herein in their entirety by reference.

FIELD OF THE INVENTION

The present invention relates to a *Cinnamomum subavenium* extract. In particular, the present invention relates to a supercritical carbon dioxide extract of *C. subavenium*, and the preparation process and the uses thereof. The *C. subavenium* supercritical extract is effective in anti-human urothelial carcinoma.

BACKGROUND OF THE INVENTION

*Cinnamomum subavenium* belongs to *Cinnamomum* genus, Lauraceae family, an endemic species grown in the forest at an altitude of 500 to 1000 meters in Taiwan, and also is nominated as *Cinnamomum randaiense*, obtuseleaf cinnamon bark, *Cinnamomum osmophloeum*, etc. It is also called as fragrant cinnamon because of its barks and leaves having fragrance. The volatile oil refined from barks of *C. subavenium* may be the essence material for cosmetics, and the leaf oil refined from leaves thereof may be the raw material for food and cigarettes, or pesticides. In traditional Chinese medicine, *C. subavenium* also is used to treat a various of diseases, such as stomachache, chest pain, abdominal pain, hernia, diarrhea, rheumatism, nausea, vomiting and so on.

Taiwan patent publication No. 200924788 discloses a pesticide combination, including *C. osmophloeum* essence oil and other essence oils for food industries and for bacteriostatic activity. That patent application only discloses the formulation made by essence oils containing *C. osmophloeum* essence oil, whereas it does not disclose the extraction method of *C. osmophloeum* essence oil and the components therein.

Taiwan patent publication No. 200914036 discloses a skin-used agent for prevent biting midges, including *C. osmophloeum*, betel nut and other major components. However, it does not disclose the preparation method of *C. osmophloeum* and the components contained therein.

Since there is not the components in *C. subavenium* and its preparation method disclosed in the prior art, it is impossible for one skilled in the art to use the components of *C. subavenium* in the medicines, cosmetics and other fields.

It is therefore attempted by the applicant to deal with the above situation encountered in the prior art.

SUMMARY OF THE INVENTION

For extracting the various components from *C. subavenium*, avoiding the use of organic solvents and reducing energy consumed in the extraction process, *C. subavenium* is extracted by using supercritical $CO_2$, by the inventors of the present invention, to obtain the plural compounds wherein subamolide A ([(3Z,4R,5R)-3-tetradecylidene-4-hydroxy-5-methoxy-5-methylbutanolide]) is the major component. *C. subavenium* supercritical $CO_2$ extract can be effectively in inhibiting the growth of urothelial carcinoma and treating cancers. In addition, the combination of alkylating agent (e.g. cisplatin (cis-diamminedichloridoplatinum; "CDDP")) (or nucleoside analog (e.g. gemcitabine (4-amino-1-(2-deoxy-2, 2-difluoro-β-D-erythro-pentofuranosyl)-pyrimidin-2(1H)-on; "Gem")) with *C. subavenium* supercritical $CO_2$ extract or the combination of alkylating agent (or nucleoside analog) with subamolide A would synergistically inhibit the growth of urothelial carcinoma. Therefore, alkylating agent and *C. subavenium* supercritical $CO_2$ extract (or subamolide A) can be prepared as a pharmaceutical composition, and nucleoside analog and *C. subavenium* supercritical $CO_2$ extract (subamolide A) can be prepared as another one, and both pharmaceutical compositions are used for treating human urothelial carcinoma or cancers relevant to the urinary system.

The present invention provides a preparation method for *C. subavenium* extract, including steps of: (a) drying *C. subavenium* plant; (b) pulverizing the plant into plural particles; and (c) extracting the plural particles with supercritical $CO_2$ to obtain the *C. subavenium* extract including subamolide A.

Preferably, the step (a) further includes step of (a1) drying the stem of *C. subavenium* plant. The step (c) is performed at a pressure of 150 to 350 bar, a temperature of 45° C. to 55° C., a flow rate of the supercritical $CO_2$ from 4 to 6 L/hr and a packing density of material between 250 g/L and 320 g/L. In some embodiments, the step (c) is further performed at 250 bar, 45° C., the flow rate of 4 L/hr and the packing density of material of 320 g/L.

The present invention further provides a pharmaceutical composition of *C. subavenium* extract for treating cancer cells and/or growth inhibition of the cancer cells, and the pharmaceutical composition includes: a first component having subamolide A; and a second component being selected from a group consisting of monoterpene, sesquiterpene, sesquiterpene derivative, saturated fatty acid, butanolide, phytosterol, triterpene, phytosterone and a combination thereof.

Preferably, (1) monoterpene includes but not limit to eugenol; (2) sesquiterpine includes but not limit to α-cubebene, α-bergamotene, trans-α-bergamotene, γ-elemene, β-acoradene, α-zingiberene, cis-α-bisabolene, β-bisabolene, β-curcumene, δ-amorphene and trans-α-bisabolene; (3) sequiterpene derivative includes but not limit to cedr-8-ene, α-curcumene, nerolidol, caryophyllene oxide, humulene-1, 2-epoxide, cubenol, τ-cadinol, α-cadinol, epi-β-cadinol, epi-β-bisabolol, epi-α-bisabolol, α-bisabalol and 1,10-dihydro nootkatone; (4) saturated fatty acid includes but not limit to ethyl palmitate; (5) butanolide includes but not limit to isolinderanolide B, linderanolide B and secosubamolide; (6) phytosterol includes but not limit to β-sitosterol and γ-sitosterol; (7) triterpene includes but not limit to betulin; and (8) phytosterone includes but not limit to sitostenone.

The present invention further provides a pharmaceutical composition, including: subamolide A with a first effective amount; and an ingredient with a second effective amount and being an alkylating agent or a nucleoside analog.

Preferably, subamolide A is a component of a supercritical $CO_2$ extract of *C. subavenium* or is a component of a methanol (MeOH) extract thereof. Alkylating agent includes but not limit to cisplatin, carboplatin (cis-diammine(1,1-cyclobutanedicar-boxylato)platinum (II)) and oxaliplatin ([(1R,2R)-cyclohexane-1,2-diamine]-(ethanedioato-O',O')platinum (II)), and nucleoside analog includes but not limit to deoxyadenosine analog, deoxycytidine analog, deoxyguanosine analog, deoxythymidine analog, deoxyuridine analog, 6-thiohypoxanthine and fluorouracil. One of the deoxycytidine analog is Gem.

The above objectives and advantages of the present invention will become more readily apparent to those ordinarily skilled in the art after reviewing the following detailed descriptions and accompanying drawings.

BRIEF DESCRIPTION OF THE DRAWINGS

FIG. 4(*b*) is a diagram showing the intracellular reactive oxygen species (ROS) M1 ratio after the subamolide A treatment on NTUB1 and SV-HUC-1 cells.

FIGS. 5(*b*) and 5(*c*) respectively are the diagrams showing the fold of changes of (b) Bax/Bcl-2 ratio and (c) cytochrome c after the subamolide A treatment on NTUB1 cells.

FIGS. 7(*c*) and 7(*d*) respectively are the diagrams showing (c) the cellular viability and (d) the CI of the combinational cytotoxic effect of subamolide A with Gem on NTUB1 cells for 24, 48 and 72 hours. CI is obtained from the median-effect analysis performed by the computer software Calcusyn™.

DETAILED DESCRIPTION OF THE PREFERRED EMBODIMENT

Figure 1:
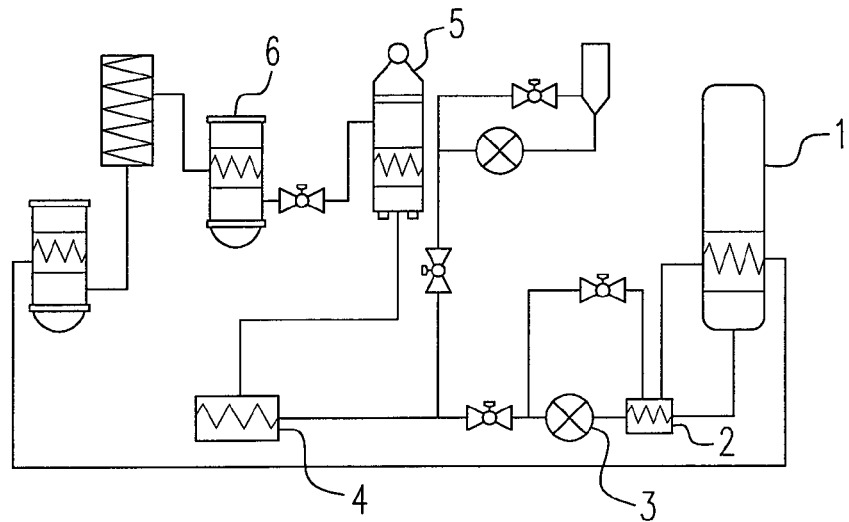
FIG. 1 is a diagram showing the apparatus for preparing *C. subavenium* supercritical $CO_2$ extract in the present invention.
Figure 2:
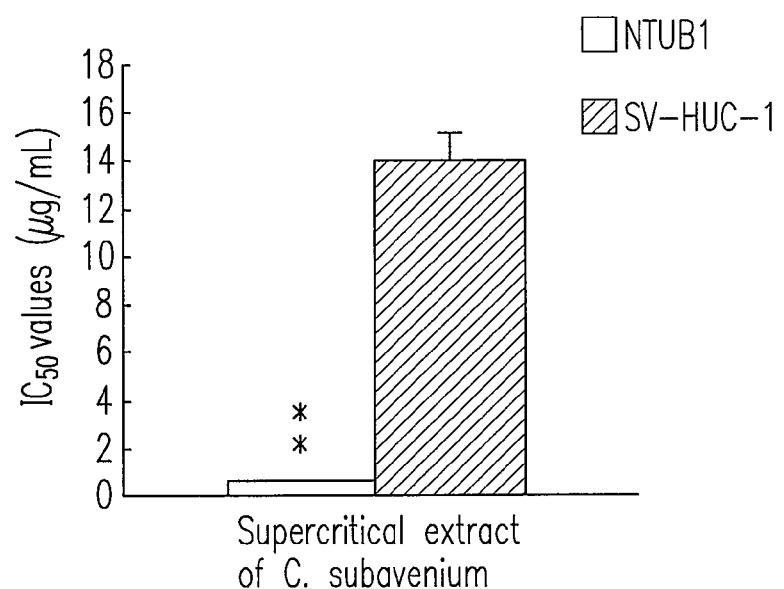
FIG. 2 is a diagram showing the cytotoxicity of *C. subavenium* supercritical $CO_2$ extract on human urothelial carcinoma cell line NTUB1 and normal urothelial cell line SV-HUC-1.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiment

*C. subavenium* extract (or nominated as *C. subavenium* MeOH extract) or *C. subavenium* supercritical $CO_2$ extract in the present invention can be used in inhibiting the growth of urothelial carcinoma and treating cancers. Alternatively, the major component, subamolide A, in *C. subavenium* extract or *C. subavenium* supercritical $CO_2$ extract can be prepared as an anticancer pharmaceutical extract. Alternatively, an effective amount of subamolide A and an effective amount of other ingredient also can be prepared as an anticancer pharmaceutical extract.

*C. subavenium* extract or *C. subavenium* supercritical $CO_2$ extract is able to synergistically inhibit the growth of urothelial carcinoma with an alkylating agent (an anticancer drug). Alternatively, subamolide A in *C. subavenium* extract or *C. subavenium* supercritical $CO_2$ extract is able to synergistically inhibit the growth of urothelial carcinoma with the alkylating agent.

*C. subavenium* extract or *C. subavenium* supercritical $CO_2$ extract is able to synergistically inhibit the growth of urothelial carcinoma with a nucleoside analog (an anticancer drug). Alternatively, subamolide A in *C. subavenium* extract or *C. subavenium* supercritical $CO_2$ extract is able to synergistically inhibit the growth of urothelial carcinoma with the nucleoside analog.

The terms, e.g. "extract", "compound", "alkylating agent", "analog", "pharmaceutical composition", "extract" and so on, herein have an effective amount upon usage, indicating an minimum effective amount for cytotoxicity, an effective amount within a scope or an maximum effective amount.

Alkylating agent includes but not limit to cisplatin, carboplatin and oxaliplatin, nucleoside analog includes but not limit to deoxyadenosine analog, deoxycytidine analog (e.g. Gem), deoxyguanosine analog, deoxythymidine analog, deoxyuridine analog, 6-thiohypoxanthine and fluorouracil, etc.

Experiments and Results:

I. Preparation and Analysis of *C. Subavenium* Supercritical $CO_2$ Extract

*C. subavenium* supercritical $CO_2$ extract of the present invention was made by extracting *C. subavenium* with supercritical $CO_2$. *C. subavenium*'s stems could be adopted as the material for extraction. First, the dried stems of *C. subavenium* (5 kg) were mechanically or physically pulverized as particles with average diameter of 1~2 mm. Next, the experiment design was performed by using the orthogonal array of Taguchi methodology. The orthogonal array L9($3^4$) was selected for permutation and combination in the present invention, and 4 control factors were determined. Control factor A was extraction pressure, control factor B was extraction temperature, control factor C was flow rate of supercritical $CO_2$ fluid mass, and control factor D was packing density of material. The parameters for determining each control factor were described as follows. Extraction pressure was 150, 250 and 350 bar respectively, extraction temperature was 45, 50 and 55° C. respectively, flow rate of supercritical $CO_2$ fluid mass was 4, 5 and 6 L/hr respectively, and packing density of material was 250, 285 and 320 g/L respectively.

Next, please refer to apparatus diagram in FIG. 1, the pulverized *C. subavenium* particles were disposed in supercritical extraction vessel 5, and solid extraction was processed with supercritical $CO_2$ fluid. After $CO_2$ within the $CO_2$ reservoir 1 was pre-cooled at pre-cooler 2 and then was transmitted through high-pressure diaphragm pump 3 and heater 4, $CO_2$ entered into supercritical extraction vessel 5 by setting the aforementioned control factors (operation pressure of 150~350 bar, temperature of 45° C.~55° C., flow rate of 4 L/hr~6 L/hr). *C. subavenium* supercritical $CO_2$ extract post the solid extraction and the supercritical $CO_2$ fluid were conducted into gas-liquid separator 6, and *C. subavenium* supercritical $CO_2$ extract was harvested at the bottom outlet of gas-liquid separator 6. The phase of supercritical $CO_2$ fluid was changed as gas to reduce the solubility of *C. subavenium* supercritical $CO_2$ extract, so that *C. subavenium* supercritical $CO_2$ extract was separated from supercritical $CO_2$ fluid and gas-liquid separation was achieved. The gaseous $CO_2$ was pressured and sent to $CO_2$ reservoir 1 for recycling.

*C. subavenium* supercritical $CO_2$ extract was analyzed to afford 34 components (Table 1) using gas chromatography-mass spectrometry (GC-MS) known by one skilled in the art. Components in Table 1 can be divided as monoterpene (e.g. eugenol), sesquiterpine (e.g. α-cubebene, α-bergamotene, trans-α-bergamotene, γ-elemene, β-acoradene, α-zingiberene, cis-α-bisabolene, β-bisabolene, β-curcumene, δ-amorphene and trans-α-bisabolene), sequiterpene derivative (e.g. cedr-8-ene, α-curcumene, nerolidol, caryophyllene oxide, humulene-1,2-epoxide, cubenol, τ-cadinol, α-cadinol, epi-β-cadinol, epi-β-bisabolol, epi-α-bisabolol, α-bisabalol and 1,10-dihydro nootkatone), saturated fatty acid (e.g. ethyl palmitate), butanolide (e.g. isolinderanolide B, linderanolide B, secosubamolide and subamolide A), phytosterol (e.g. β-sitosterol and γ-sitosterol), triterpene (e.g. betulin) and phytosterone (e.g. sitostenone).

Since *C. subavenium* supercritical $CO_2$ extract are extracted from *C. subavenium*, the types of components, and the species and amounts of compounds are influenced by factors such as climate, temperature, moisture, rainwater, cultivation environment, soil, harvest and so on. Therefore, the components and ratios of *C. subavenium* supercritical $CO_2$ extracts are diverse with the batches. One skilled in the art can arbitrarily prepare the pharmaceutical extract including subamolide A and/or other ingredients in accordance with the types and ingredient of these components based on the present invention.

TABLE 1

Analysis of components in *C. subavenium* supercritical $CO_2$ extract using GC-MS

| No. | Components | KI[a] | KI[b] | Percentage (%)[c] | Identification[d] |
|---|---|---|---|---|---|
| 1 | Eugenol | 1341 | 1341 | 1.29 | MS, KI |
| 2 | α-Cubebene | 1363 | 1360 | 0.48 | MS, KI |
| 3 | Cedr-8-ene | 1401 | 1405 | 0.28 | MS, KI |
| 4 | α-Bergamotene | 1394 | 1394 | 0.17 | MS, KI |
| 5 | trans-α-Bergamotene | 1423 | 1423 | 0.68 | MS, KI |
| 6 | γ-Elemene | 1438 | 1433 | 1.31 | MS, KI |
| 7 | β-Acoradiene | 1442 | 1440 | 0.36 | MS, KI |
| 8 | α-Curcumene | 1470 | 1470 | 6.27 | MS, KI |
| 9 | α-Zingiberene | 1495 | 1495 | 1.66 | MS, KI |
| 10 | Cis-α-bisabolene | 1494 | 1494 | 0.66 | MS, KI |
| 11 | β-Bisabolene | 1500 | 1500 | 4.66 | MS, KI |
| 12 | β-Curcumene | 1503 | 1503 | 0.56 | MS, KI |
| 13 | δ-Amorphene | 1499 | 1499 | 1.03 | MS, KI |
| 14 | trans-α-Bisabolene | 1523 | 1530 | 1.79 | MS, KI |
| 15 | Nerolidol | 1549 | 1550 | 0.36 | MS, KI |
| 16 | Caryophyllene oxide | 1551 | 1549 | 0.86 | MS, KI |
| 17 | Humulene-1,2-epoxide | 1581 | 1580 | 0.73 | MS, KI |
| 18 | Cubenol | 1603 | 1601 | 2.79 | MS, KI |
| 19 | τ-Cadinol | 1626 | 1625 | 2.00 | MS, KI |
| 20 | α-Cadinol | 1628 | 1628 | 0.84 | MS, KI |
| 21 | epi-β-Cadinol | 1641 | 1644 | 1.74 | MS, KI |
| 22 | epi-β-Bisabolol | 1669 | 1672 | 14.79 | MS, KI |
| 23 | epi-α-Bisabolol | 1688 | 1687 | 0.78 | MS, KI |
| 24 | α-Bisabalol | 1690 | 1691 | 0.57 | MS, KI |
| 25 | 1,10-Dihydro nootkatone | 1756 | 1761 | 0.63 | MS, KI |
| 26 | Ethyl palmitate | 1982 | 1983 | 0.61 | MS, KI |
| 27 | Isolinderanolide B | 2291 | — | 10.29 | MS |
| 28 | Linderanolide B | 2326 | — | 1.22 | MS |
| 29 | Secosubamolide | 2410 | — | 3.42 | MS |
| 30 | Subamolide A | 2427 | — | 35.10 | MS, ST |
| 31 | β-Sitosterol | 3317 | — | 1.28 | MS |
| 32 | γ-Sitosterol | 3363 | — | 0.39 | MS |
| 33 | Betulin | 3380 | — | 0.13 | MS |
| 34 | Sitostenone | 3487 | — | 0.30 | MS |

[a]Kovats index relative to n-alkanes ($C_{10}$-$C_{40}$) on a DB-5MS column.
[b]Reference kovats index on a DB-5MS column.
[c]Relative percentage calculated by integrated peak area in Thermo Xcalibur ™ data analysis program.
[d]Identification based on comparison of the mass spectrum, co-injected with standard & Kovats index on a DB-5MS column in reference.

It could be known from Table 1 that subamolide A ([(3Z, 4R,5R)-3-tetradecylidene-4-hydroxy-5-methoxy-5-methylbutanolide; formula I; 35.1% of percentage) was the major component in *C. subavenium* supercritical $CO_2$ extract.

(Formula I)

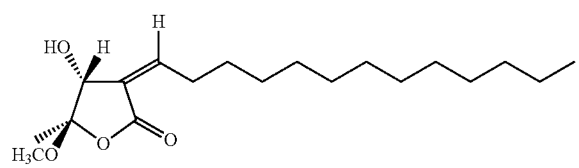

The experimental design in the present invention was processed using the orthogonal array L9($3^4$) of Taguchi methodology to establish the best operational condition with extraction pressure of 150 bar, extraction temperature of 45° C., flow rate of supercritical $CO_2$ fluid mass of 4 L/hr and packing density of material of 250 g/L. It could be known from the signal to noise ratio (SN ratio) that the major factors to influence the yield of *C. subavenium* supercritical $CO_2$ extract sequentially were flow rate of supercritical $CO_2$ fluid mass, extraction temperature, packing density of material and extraction pressure, and the best predicted operational condition were extraction pressure of 250 bar, extraction temperature of 45° C., flow rate of supercritical $CO_2$ fluid mass of 4 L/hr and packing density of material of 320 g/L. Yields obtained from the above two operational conditions were 7.7% and 7.8% respectively, indicating that the operational conditions established from two experimental methods were similar, and confirming that the difference between the experimental result and the predicted SN ratio was less than 5. That is, the selected experimental condition was established, and the yield of supercritical extraction was 5.39% to be better than yield of organic solvent extraction of 1.54%.

Cytotoxicity assay was performed by using *C. subavenium* supercritical $CO_2$ extract obtained according to the preparation method mentioned above. Please refer to FIG. 2, it was found that *C. subavenium* supercritical $CO_2$ extract showed the best cytotoxicity ($IC_{50}$=0.67±0.02 μg/mL) to human urothelial carcinoma cell line NTUB1 and the cytotoxicity ($IC_{50}$=14.1±1.15 μg/mL) to normal urothelial cell line SV-HUC-1. *C. subavenium* supercritical $CO_2$ extract selectively functioned on NTUB1 carcinoma cells rather than the normal cells.

II. Preparation of *C. Subavenium* Extract

Additionally, subamolide A (purity>90%) was isolated from the stems of *C. subavenium*. Briefly, the air-dried stems were extracted with MeOH at room temperature. The MeOH extract, obtained by concentration under reduced pressure, was suspended in H$_2$O and then partitioned with chloroform (CHCl$_3$) to yield fractions soluble in CHCl$_3$ and H$_2$O. The CHCl$_3$ soluble fraction was chromatographed over silica gel using n-hexane-ethyl acetate (EtOAc)-MeOH mixtures as eluents and separated into five fractions. Fraction 2 was re-subjected to silica gel column chromatography and purified by preparative thin layer chromatography using n-hexane-EtOAc to yield subamolide A. Subamolide A was dissolved in dimethyl sulfoxide (DMSO) and stored at −20° C.

III. Statistical Analysis

Data of the following experimental results were expressed as means±SD. Statistical analyses were performed using the Bonferroni t-test method after ANOVA for multigroup comparison and the Student's t-test method for two group comparison, with *$P<0.05$, $P<0.01$ and *$P<0.001$ were considered to be statistically significant.

IV. Cytotoxic Effect of Subamolide A on Various Cell Lines

Cellular cytotoxicity of tested compounds was performed by using a MTT (3-[4,5-dimethylthiazol-2-yl]-2,5-diphenyltetrazolium bromide) assay. Briefly, the cells were plated with a density of $1\times10^3$ cells/well in 96-well plates and incubated at 37° C. overnight before drug treatment. Cells were then cultured in the absence or presence of various concentrations (0.3, 1, 3, 6, 9, 12, 15 and 20 μM) of subamolide A at 37° C. for 72 hours. Subsequently, 50 μL of MTT (2 mg/mL in PBS) was added to each well and allowed to react for another 4 hours. Following centrifugation at 1000×g for 10 minutes, media were removed and 150 μL DMSO were added to each well. The proportions of surviving cells were determined by absorbance spectrometry at 540 nm using a microplate reader. The cell viability was expressed as the survival ratio to the un-treated control. The IC$_{50}$ values of each group were calculated by the median inhibitory analysis and presented as means±SD. The combinational effects of two compounds were analyzed by median-effect analysis. To evaluate the combined effects in growth inhibition, a corresponding combination index (CI) was adopted for the measurement. The combination index of <1, =1, or >1 denotes synergic, additive, or antagonistic effect, respectively.

Figure 3:
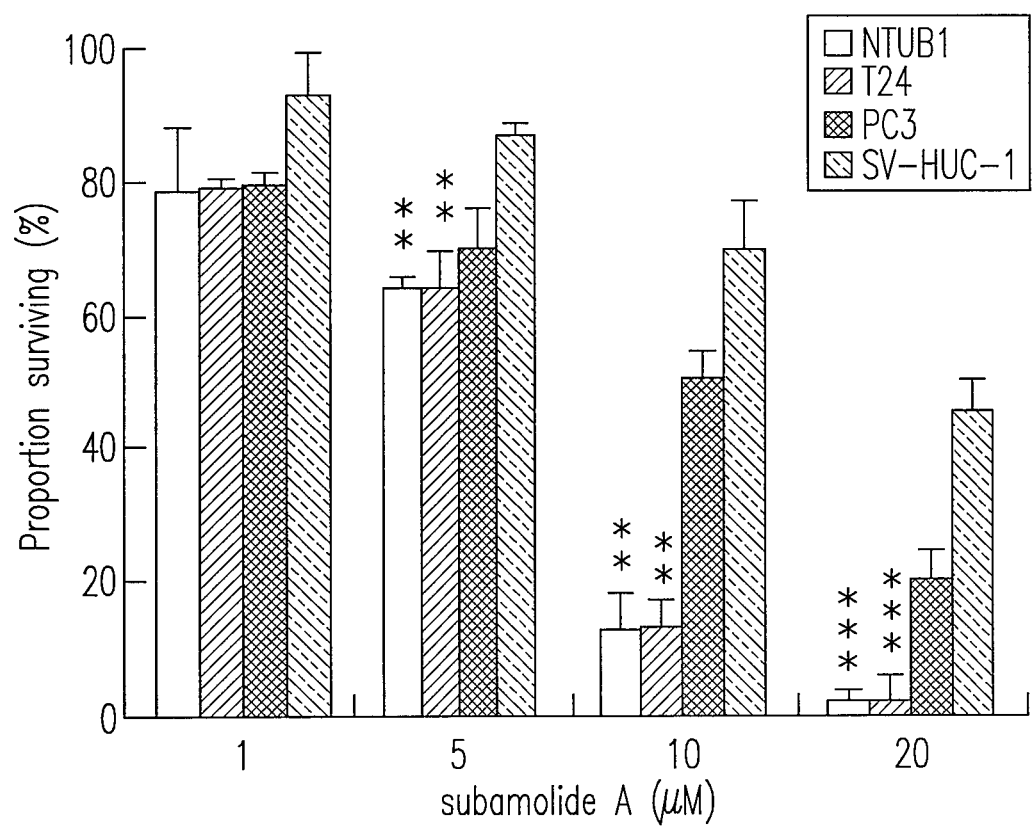
FIG. 3 is a diagram showing the cellular viability of subamolide A on human urothelial carcinoma cell lines NTUB1 and T24, human prostate cancer cell line PC3, and normal urothelial cell line SV-HUC-1.

Please refer to FIG. 3, which is the diagram showing the cellular cytotoxicity of subamolide A on human urothelial carcinoma cell line. Subamolide A showed a significant reduction of growth in urothelial carcinoma cells NTUB1 (IC$_{50}$=7.26±0.67 μM) and T24 (IC$_{50}$=7.60±0.96 μM) as compared to prostate cancer cells PC3 (IC$_{50}$=10.10±0.59 μM) and immortalized human uroepithelial cell SV-HUC-1 (IC$_{50}$=18.10±1.03 μM), respectively. NTUB1 was chose to study the anticancer mechanism of subamolide A in the following experiments. As shown in FIG. 3, subamolide A caused a dose-dependent reduction of growth in NTUB1 and T24 cells after 72 hours while less cytotoxic effect was observed in PC3 and SV-HUC-1 cells.

V. Subamolide A Induces Apoptosis in NTUB1 Cells

Figure 4A:
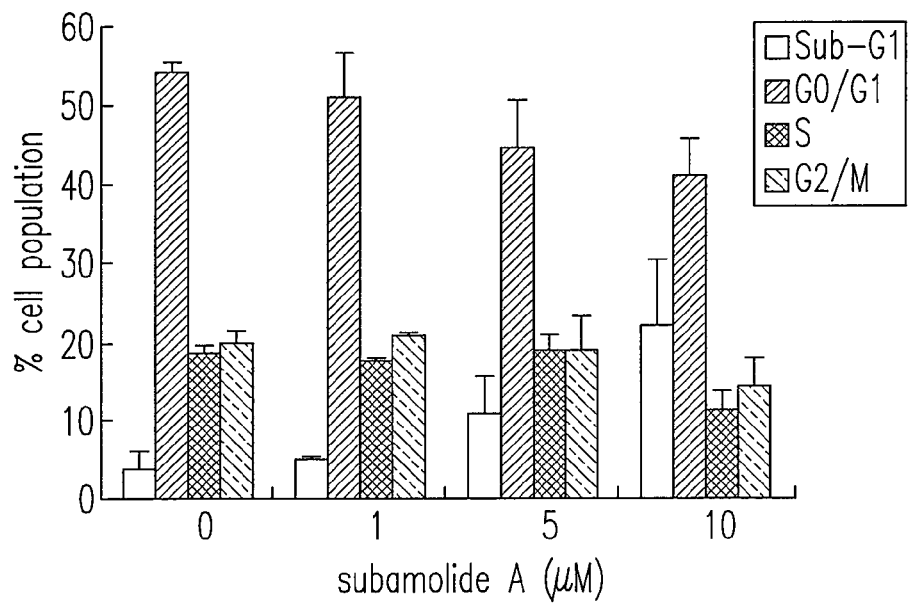
FIG. 4(*a*) is a diagram showing the percentage of each cell cycle phase after the subamolide A treatment on NTUB1 cells.
Figure 4B:
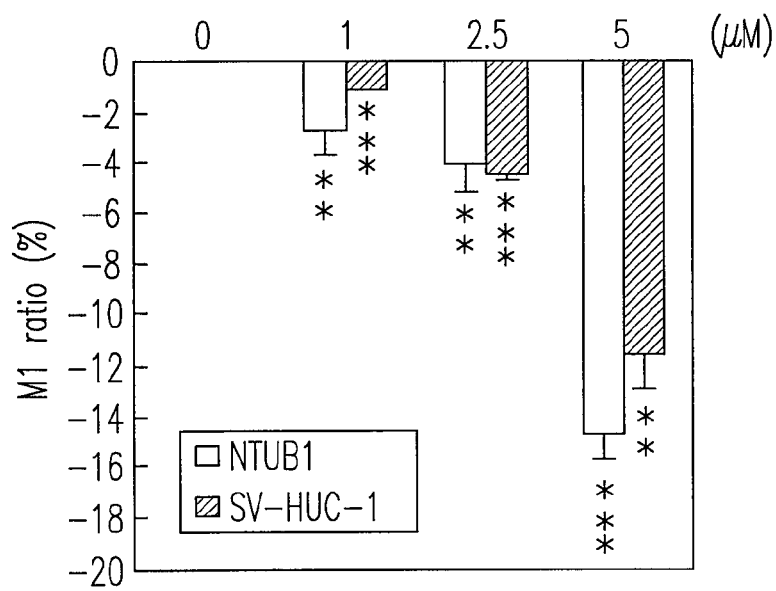

Please refer to FIG. 4($a$), after NTUB1 cells ($3\times10^5$ cells/well) were treated with 1, 5 and 10 μM of subamolide A for 24 hours, the increased sub-G1 apoptotic fraction was observed in a dose-dependent fashion (5%, 10.8%, and 21.9%, respectively) using flow cytometry when compared with the untreated control.

VI. Quantitative Analysis of Intracellular Reactive Oxygen Species (ROS)

Production of ROS was analyzed by flow cytometry. Briefly, cells were plated in 6-well plates, and dichlorofluorescein diacetate (DCFH-DA, 10 μl) were added to the treated cells 30 minutes prior to harvest. The cells were collected by trypsinization and washed with PBS. The green fluorescence of intracellular DCF (2',7'-dichlorofluorescein) was then analyzed by FACScan™ flow cytometer with a 525-nm band pass filter. The ROS production efficiency (M1 ratio) was calculated as "[counts of treated sample in M1−counts of control in M1]/counts of control in M1×100".

ROS causes a wide range of adaptive cellular responses ranging from transient growth arrest to permanent growth arrest, apoptosis, or necrosis, depending on the amount of ROS. Here, the effect of subamolide A on the intracellular ROS level in NTUB1 and SV-HUC-1 cells were evaluated.

Please refer to FIG. 4($b$), the ROS M1 ratio of NTUB1 cells was −14.7±0.99%, while that of SV-HUC-1 cells was −11.6±1.41% at 10 μM of subamolide A treatment when compared with the control cells. Subamolide A caused a significant reduction in intracellular ROS level (M1 ratio) but similar changes were observed in both cell lines with increased concentrations. That is, subamolide A reduced the ROS production in NTUB1 and SV-HUC-1 cell lines. The results suggest that alterations in ROS levels do not differentiate cytotoxicity in these cell systems.

VII. Mitochondrial Apoptotic Pathway by Mitochondrial Membrane Potential (MMP; Δψm) measurement MMP levels were measured by the lipophilic cation JC-1 (5,5',6,6'-tetrachloro-1,1',3,3',-tetraethylbenzimidazolylcarbocyanine iodide) fluorescent dye. Briefly, cells were plated and treated as the aforementioned conditions. JC-1 (1 μM) was added to the treated cells 30 minutes prior to harvest. The cells were collected by trypsinization and washed with PBS. The red (aggregated JC1; R1 region) and green (monomeric JC1; R2 region) fluorescence signals were analyzed immediately by FACScan™ flow cytometer and Cell Quest™ software.

To determine whether subamolide A induces cytotoxicity by triggering the mitochondrial apoptotic pathway, the changes of mitochondrial membrane potential (Δψm) in subamolide A-treated NTUB1 cells were measured. It was that subamolide A converted JC-1 from aggregate form (red fluorescence; R1) to monomer form (green fluorescence; R2) indicated the disruption of mitochondrial function at 10 μM of subamolide A treatment (3.52% versus 52.04%).

Figure 5A:
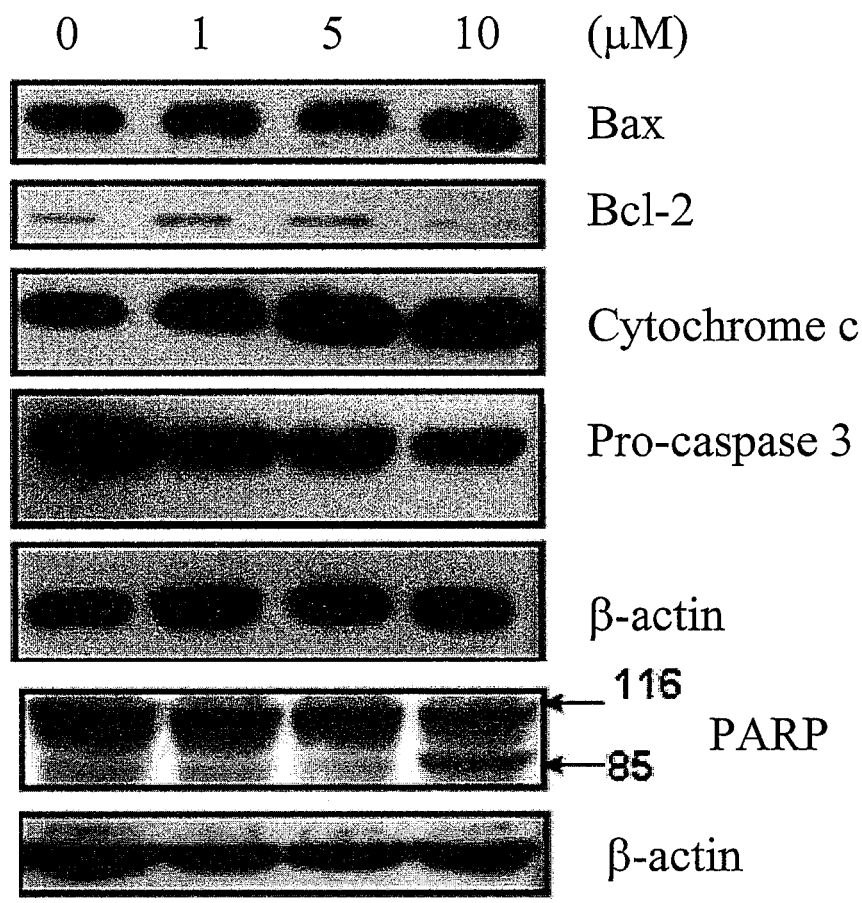
FIG. 5(*a*) is an immunoblotting spectrum showing the cellular protein expressions after the subamolide A treatment on NTUB1 cells.
Figure 5B:
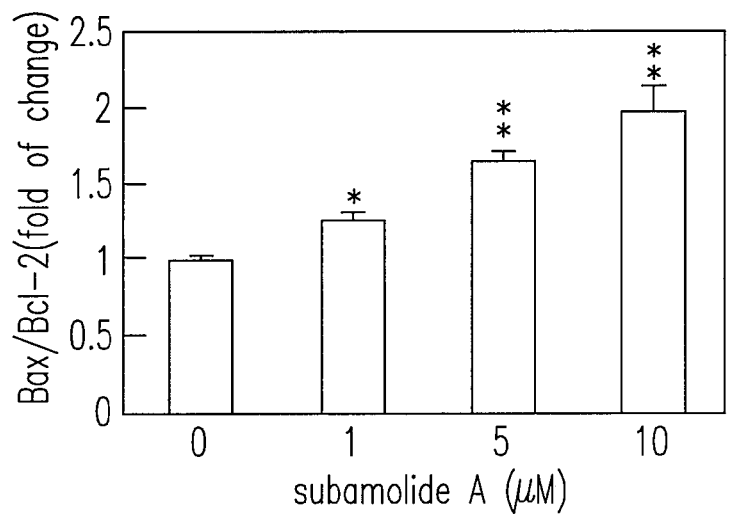
Figure 5C:
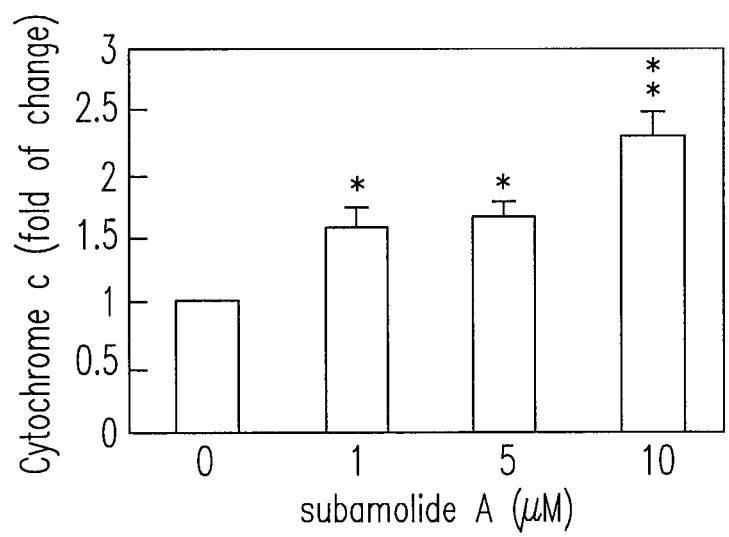

In addition, please refer to FIGS. 5($a$) and 5($b$), at a reduced Δψm, subamolide A up-regulated Bax and down-regulated of Bcl-2 expression, resulting in a two-fold increase of Bax/Bcl-2 ratio at 10 μM of subamolide A. Concomitantly, cytochrome c was released from the mitochondria to the cytosol (to 2.3 folds at 10 μM of subamolide A) (FIG. 5($c$)). In addition, decreased pro-caspase 3 and the 116 kDa full length PARP (poly (ADP-ribose) polymerase) proteins were observed with the increased concentration of subamolide A, indicating that caspase 3 is activated and cleaved by PARP and demonstrating that subamolide A-induced apoptosis is through activating mitochondrial apoptotic signaling pathways.

VIII. Effect of Subamolide A-Induced Apoptosis in NTUB1 Cells

Figure 6A:
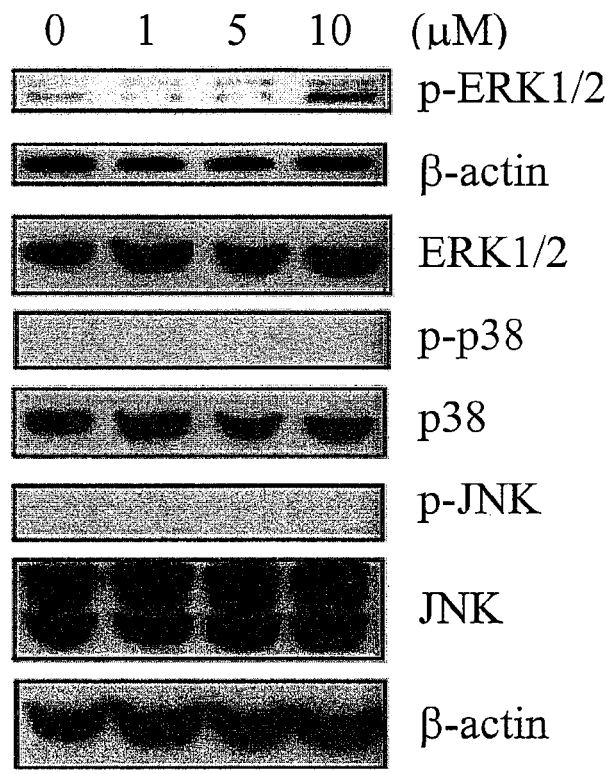
FIGS. 6(*a*) and 6(*b*) are the immunoblotting spectra showing the protein expressions of NTUB1 cells post the subamolide A treatment.
Figure 6B:
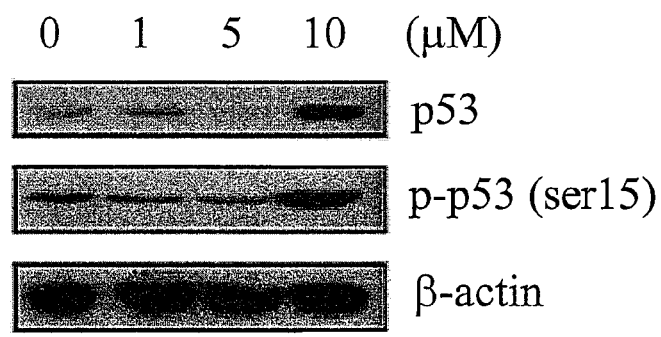

Please refer to the immunoblotting spectrum in FIG. 6($a$), ERK1/2 (extracellular signal-regulated kinases 1 and 2) but not p38 or JNK (c-Jun N-terminal kinase) was specifically activated by 10 μM of subamolide A at 24 hours in NTUB1 cells. Furthermore, subamolide A induced p53 protein and phosphorylation of p53 at serine 15 (p-p53) in NTUB1 cells, suggesting that p53 is critical for the induction of apoptosis mediated by subamolide A (FIG. 6($b$)).

Figure 7A:
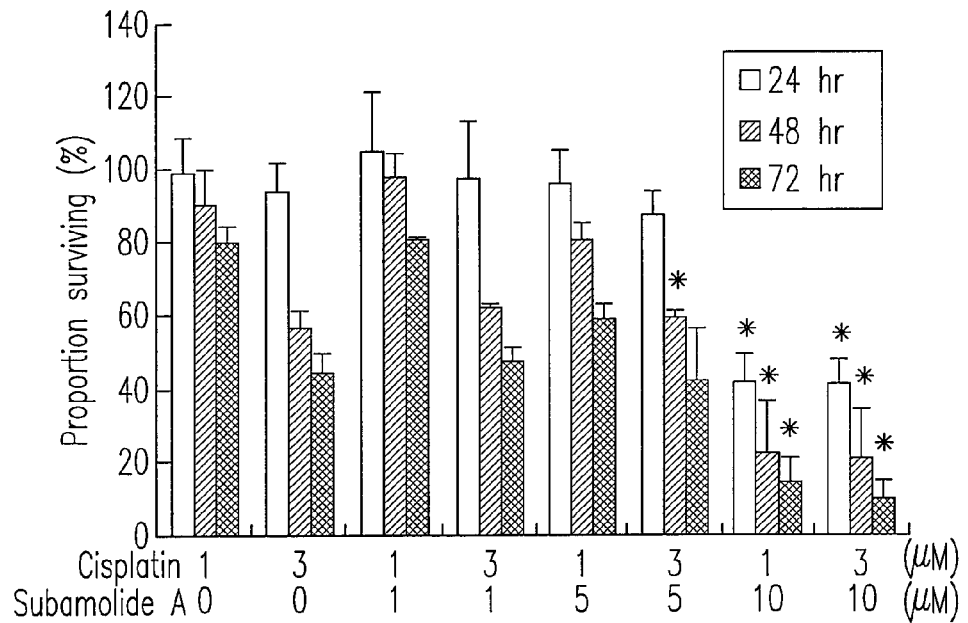
FIGS. 7(*a*) and 7(*b*) respectively are the diagrams showing (a) the cellular viability and (b) the combination index (CI) of the combinational cytotoxic effect of subamolide A with CDDP on NTUB1 cells for 24, 48 and 72 hours. CI is obtained from the median-effect analysis performed by the computer software Calcusyn™.
Figure 7B:
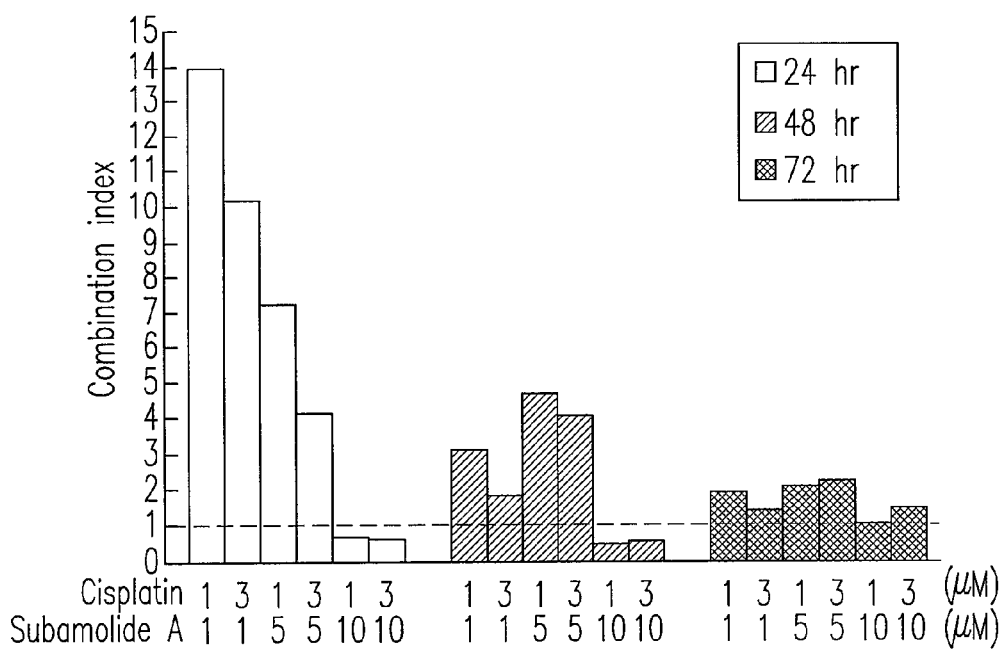
Figure 7C:
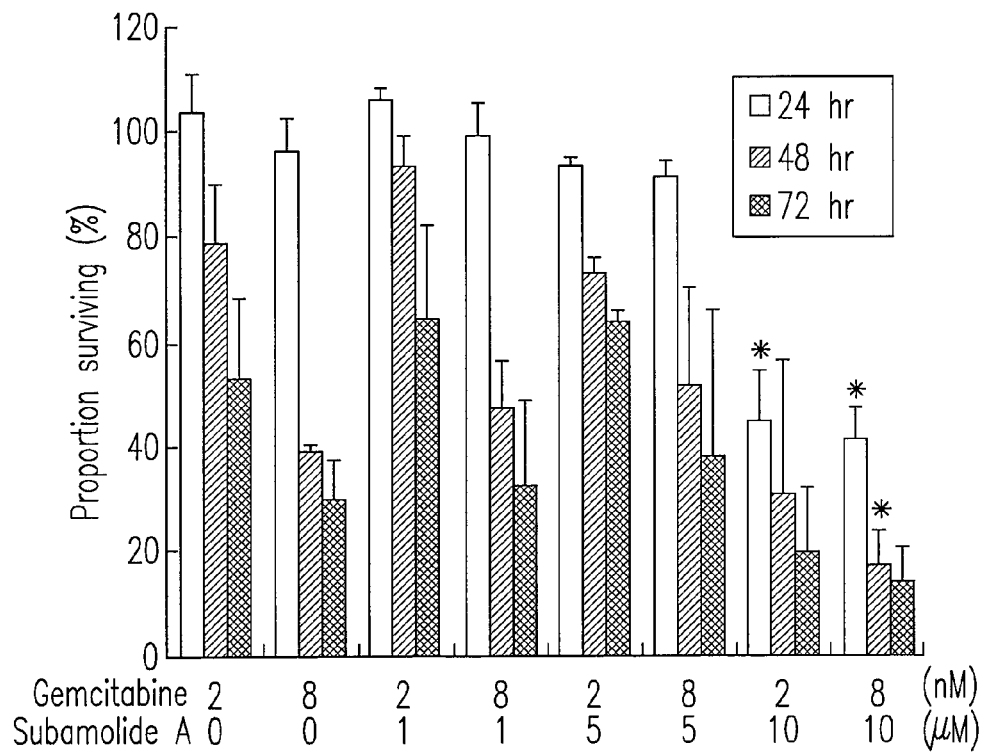
Figure 7D:
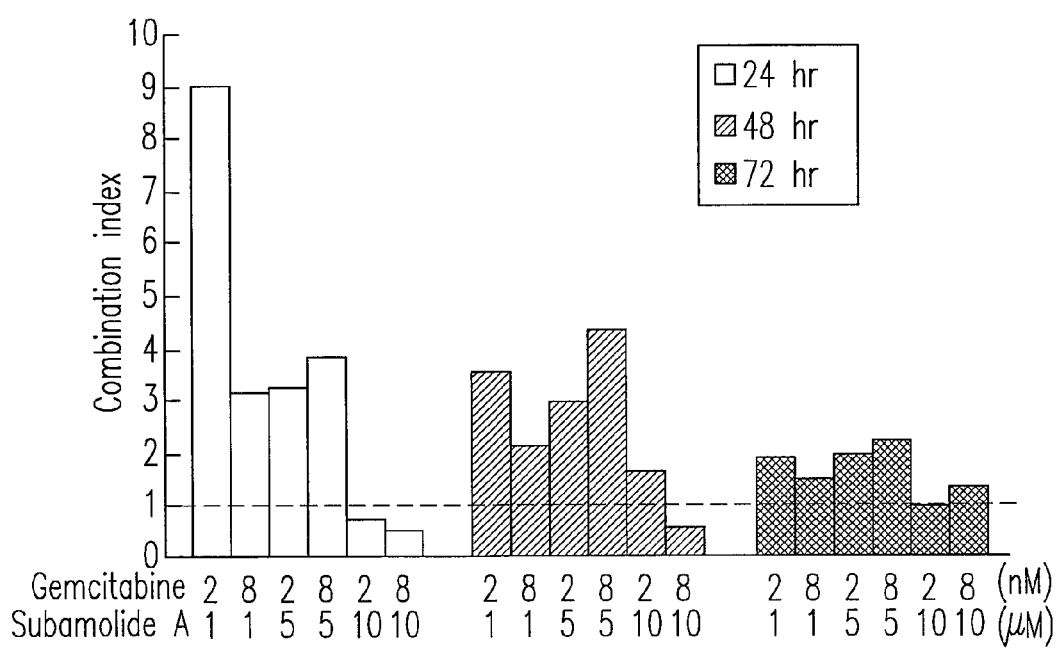

IV. Combinational Cytotoxicity of Subamolide A with Cisplatin or Gemcitabine on NTUB1 Cells Cisplatin (CDDP) and gemcitabine (Gem) are commercialized chemotherapeutic agents, in which the IC$_{50}$ values of CDDP and Gem to NTUB1 cells (a seeding number of 1×10³ cells/well at beginning) are 3 μM and 8 nM at 72 hours (data not shown). Please refer to FIG. 7(a), a sub-cytotoxic concentration of CDDP (1 and 3 μM) (or Gem (2 and 8 nM)) was co-treated with various doses of subamolide A (0, 1, 5 and 10 μM) on NTUB1 cells (a seeding number of 1×10³ cells/well at beginning) and cell viability was monitored by the MTT assay and the combination index (CI) was determined for three successive days. It was found that subamolide A showed an effective and significant inhibitory effect on the growth of NTUB1 cells with both CDDP and Gem (referring to FIGS. 7(a), 7(b), 7(c) and 7(d)), suggesting that subamolide A and CDDP (or subamolide A and Gem) shows synergism on urothelial carcinoma cells (such as NTUB1 cells).

Since subamolide A is the major component of the *C. subavenium* supercritical $CO_2$ extract, a more excellent inhibition effect would be obtained by one skilled in the art by co-treating the *C. subavenium* supercritical $CO_2$ extract containing subamolide A with CDDP (or Gem) on the urothelial carcinoma cells.

The aforementioned assay was made by combining several concentrations of subamolide A with those of CDDP (or Gem) for analyzing the synergistic effect. The concentrations of subamolide A and CDDP (or Gem) can be arbitrarily adjusted to be administered on NTUB1 cells or other cell lines or otherwise be administered on the animals with the appropriate physiological conditions (e.g. body weight, age, sex, disease, etc.) and appropriate experimental conditions by one skilled in the art. For instance, in a cellular experiment with NTUB1 cells at a density of 1×10³ cells/well, the concentration of subamolide A was adjusted as lower than 1 μM, within 1 to 10 μM, or higher than 10 μM, the concentration of CDDP was adjusted as lower than 1 μM, within 1 to 3 μM, or higher than 3 μM, and the concentration of Gem was adjusted as lower than 2 μM, within 2 to 8 μM, or higher than 8 μM. In the animal mode, (1) the appropriate amounts of subamolide A and CDDP (or Gem), (2) the appropriate amounts of the *C. subavenium* MeOH extract (containing an appropriate amount of subamolide A) and CDDP (or Gem), or (3) the appropriate amounts of the *C. subavenium* supercritical $CO_2$ extract (containing an appropriate amount of subamolide A) and CDDP (or Gem) were administered in accordance with animals' conditions, e.g. body weight, age, sex, disease, etc. Furthermore, the appropriate amounts of subamolide A (in the *C. subavenium* MeOH extract or the *C. subavenium* supercritical $CO_2$ extract) and CDDP (or Gem) administered on the human being could be calculated/reduced by one skilled in the art. The pharmaceutical composition including the appropriate amounts of subamolide A and CDDP (or Gem) could be administered on the animal cells and animals, which include human beings, rodents, other mammals and so on.

Figure 8A:
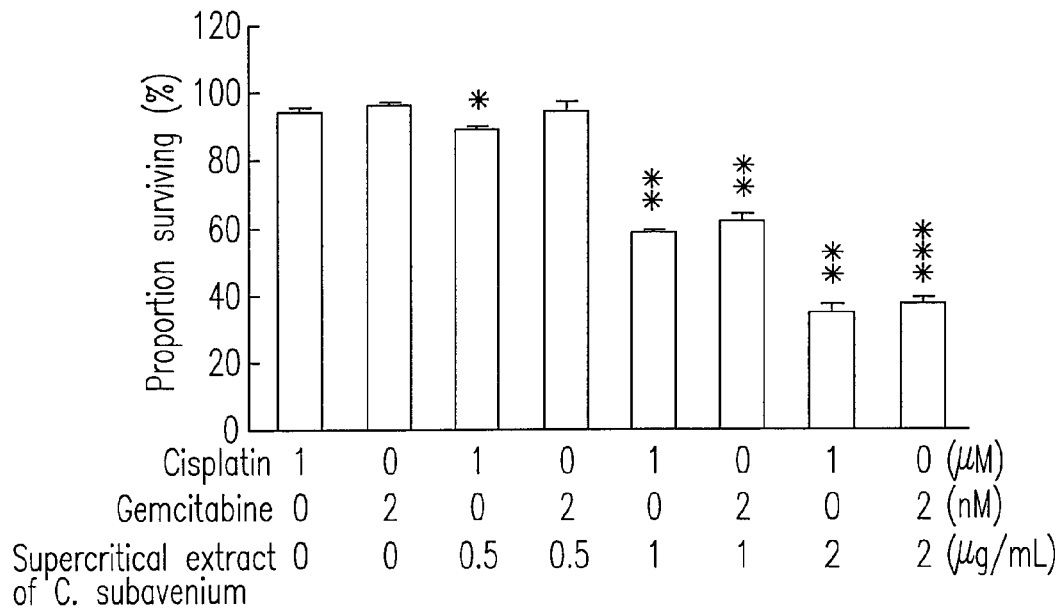
FIGS. 8(*a*) and 8(*b*) respectively are the diagrams showing (a) the cellular viability and (b) the CI of the combinational cytotoxic effect of *C. subavenium* supercritical $CO_2$ extract (containing the major component, subamolide A) with CDDP (or Gem) on NTUB1 cells for 24 hours. CI is obtained from the median-effect analysis performed by the computer software Calcusyn™.
Figure 8B:
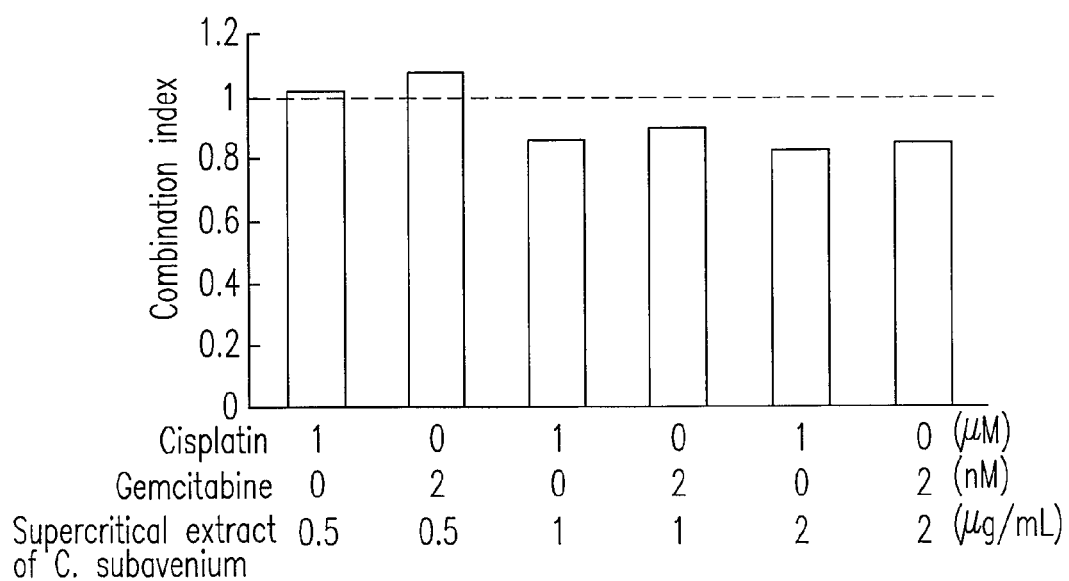

In addition, please refer to FIGS. 8(a) and 8(b), it was found that the cytotoxic activity of NTUB1 cells can be synergistically increased by the combination of the *C. subavenium* supercritical $CO_2$ extract (lower than 1 and 2 μg/mL) with CDDP (1 μM) (or Gem of 2 nM), and its synergistic effect was better than subamolide A alone.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A pharmaceutical composition, comprising:
   a subamolide A with a first effective amount; and
   an ingredient with a second effective amount and being one of an alkylating agent and a nucleoside analog.

2. The pharmaceutical composition according to claim 1, wherein the subamolide A is a component of a supercritical carbon dioxide extract of a *Cinnamomum subavenium*.

3. The pharmaceutical composition according to claim 1, wherein the subamolide A is a component of a methanol extract of a *Cinnamomum subavenium*.

4. The pharmaceutical composition according to claim 1, wherein the alkylating agent is selected from a group consisting of a cis-diamminedichloridoplatinum, a cis-diammine(1,1-cyclobutanedicarboxy-lato)platinum (II) and a [(1R,2R)-cyclohexane-1,2-diamine](ethanedioato-O',O')platinum (II).

5. The pharmaceutical composition according to claim 1, wherein the nucleoside analog is selected from a group consisting of a deoxyadenosine analog, a deoxycytidine analog, a deoxyguanosine analog, a deoxythymidine analog, a deoxyuridine analog, a 6-thiohypoxanthine and a fluorouracil.

6. The pharmaceutical composition according to claim 5, wherein the deoxycytidine analog is a 4-amino-1-(2-deoxy-2,2-difluoro-β-D-erythro-pentofuranosyl)-pyrimidin-2(1H)-on (gemcitabine).

* * * * *